United States Patent
Denda et al.

(10) Patent No.: US 6,315,980 B1
(45) Date of Patent: Nov. 13, 2001

(54) SKIN BARRIER FUNCTION RECOVERY AND PROMOTION COMPOSITION AND EVALUATION METHOD THEREOF

(75) Inventors: Mitsuhiro Denda; Toru Tsuchiya; Masahiro Tanida; Ken Shoji, all of Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 09/400,534

(22) Filed: Sep. 21, 1999

(30) Foreign Application Priority Data

Sep. 25, 1998 (JP) .................................................. 10-271692

(51) Int. Cl.⁷ .................................................. A61K 51/00
(52) U.S. Cl. .............................................................. 424/9.2
(58) Field of Search ............................... 424/9.2, 9.1, 401

(56) References Cited

U.S. PATENT DOCUMENTS 5,204,099 * 4/1993 Barbier et al. ........................ 424/401

FOREIGN PATENT DOCUMENTS 1-254628   10/1989  (JP) .

OTHER PUBLICATIONS

Pare et al., "Restraint Stress in Biomedical Research: A Review," *Neuroscience & Biobehavioral Reviews*, vol. 10, pp. 339–370, (1986).

* cited by examiner

*Primary Examiner*—Michael G. Hartley
(74) *Attorney, Agent, or Firm*—Foley & Lardner (57) ABSTRACT

A skin barrier function recovery and promotion composition containing, as an active ingredient, a fragrance which is effective when evaluated by applying a predetermined stress to a model experimental animal, in a system to which the tested fragrance is not applied, to thereby reduce the skin barrier function of the animal and using this data of the degree of recovery of the skin barrier function as an indicator and evaluating the capability by the difference between this data and data of the degree of recovery of the skin barrier function in a system to which the tested fragrance is applied.

3 Claims, 8 Drawing Sheets

SKIN BARRIER FUNCTION RECOVERY AND PROMOTION COMPOSITION AND EVALUATION METHOD THEREOF

BACKGROUND OF THE INVENTION

1. Field of the Invention

The present invention relates to a skin barrier function recovery and promotion composition and an evaluation method thereof and more specifically relates to an improvement in the effective ingredient.

2. Description of the Related Art

In recent years, the aromatherapy has been interested as a method for the treatment capable of being easily used and having relatively few side-effects. In particular, it has been noted as an effective method for the treatment of unidentified climical syndrome, autonomic imbalance, and other psychosomatic disorders due to cause of stress. There are various fragrances known as aromatherapy agents for alleviation of various symptoms. Among these, there are fragrances which are considered effective for improvement of the skin.

However, the effects thereof are vague due to the judgement of experience to a large extent. There are few fragrances which are known to possess clear specific pharmacological effects. Especially, they have not been offered as medicines or agents particularly effective for recovery or promotion of the skin barrier function.

Further, while research on the physiological action of fragrances has been relatively often carried out, there has been little research on the improvement of the skin functions by inhalation of the scent of fragrances and there has not been any objective method for evaluation of the effectiveness thereof either. Therefore, it has been difficult to find fragrances effective as agents for the recovery or promotion of the skin barrier function.

SUMMARY OF THE INVENTION

Accordingly, the objects of the present invention are to eliminate the above-mentioned problems of the prior art and to provide A skin barrier function recovery and promotion composition containing a fragrance and a simple method for evaluating the effectiveness thereof.

In accordance with the present invention, there is provided a skin barrier function recovery and promotion composition comprising (i) at least 0.01% by weight, based upon the total weight of the composition, of at least one skin barrier function recovery and promotion agent selected from the group consisting of terpinyl acetate, phenethyl alcohol, and dimethoxymethylbenzene and (ii) a cosmetically or pharmacologically acceptable carrier thereof.

In accordance with the present invention, there is also provided a skin barrier function recovery and promotion composition comprising (i) at least 0.01% by weight, based upon the total weight of the composition, of at least one skin barrier function recovery and promotion agent selected from the group valerian fragrance, violet fragrance and a rose fragrance and (ii) a cosmetically acceptable carrier thereof.

In accordance with the present invention, there is further provided a method for evaluating the effectiveness of the capability of a test fragrance to recover a skin barrier function comprising:

applying a predetermined stress to a model experimental animal, in a system to which the fragrance is not applied, to thereby reduce the skin barrier function of the animal determining the degree of recovery of the reduced skin barrier function, of which data is used as an indicator for evaluation and determining the data of the degree of recovery of the skin barrier function in a system to which the fragrance is applied, and evaluating the effectiveness from the difference of the data between the degrees of the recovery of the skin barrier functions in the two systems.

BRIEF DESCRIPTION OF THE DRAWINGS

The present invention will be better understood from the description set forth below with reference to the accompanying drawings, wherein.

DESCRIPTION OF THE PREFERRED EMBODIMENTS

The present inventors engaged in intensive studies to achieve the above object and, as a result, found that, when applying a certain stress to model experimental animals, to thereby cause a reduction of the skin barrier function of the animals, there was a significant difference in the ability to recover the skin barrier function between control animals, to which no fragrance is inhaled, and test animals, to which specific fragrances are inhaled and found that those specific fragrances are superior as skin barrier function recovery and promotion agents. The termnimals, used herein means the animals except for human beings and typically include, for example, mice, rats, guinea pigs, etc.

That is, the skin barrier function recovery and promotion composition according to the present invention contains at least 0.01% by weight, preferably 0.5% to 100% by weight, based upon the total weight of the composition, of terpinyl acetate.

Alternatively, the skin barrier function recovery and promotion composition according to the present invention contains at least 0.01% by weight, preferably 0.5% to 100% by weight, based upon the total weight of the composition, of phenethyl alcohol.

Alternatively, the skin barrier function recovery and promotion composition according to the present invention contains at least 0.01% by weight, preferably 0.5% to 100% by weight, based upon the total weight of the composition, of dimethoxymethylbenzene.

Alternatively, the skin barrier function recovery and promotion composition according to the present invention contains at least 0.01% by weight, preferably 0.5% to 100% by weight, based upon the total weight of the composition, of a valerian fragrance.

Alternatively, the skin barrier function recovery and promotion composition according to the present invention contains at least 0.01% by weight, preferably 0.5% to 100% by weight, based upon the total weight of the composition, of a sweet violet fragrance.

Alternatively, the skin barrier function recovery and promotion composition according to the present invention contains at least 0.01% by weight, preferably 2.5% to 100% by weight, based upon the total weight of the composition, of a rose fragrance.

Furthermore, the method for evaluating the effectiveness of the capability of a fragrance to recover a skin barrier function according to the present invention comprises the steps of applying a predetermined stress to a model experimental animal, in a system to which the test fragrance is not applied, then causing a reduction in the skin barrier function of the animal and using the data of the degree of recovery of the skin barrier function as an indicator and evaluating the difference with data of the degree of recovery of the skin barrier function in a system to which the tested fragrance is applied.

Further, the method for evaluating the effectiveness of the capability of a fragrance to recover a skin barrier function according to the present invention preferably includes:

(A) a step of applying stress to a mouse, rat, or guinea pig, in such a degree where a delay in the recovery of the skin barrier function is significantly recognized, whereby a reduction in a predetermined skin barrier function of an animal subjected to stress is caused;

(B) a step of measuring a transepidermal water loss (TEWL) in the reduced location at constant times; and (C) a step of comparing the data obtained at step (B) for an animal to which the test fragrance has not been applied (control) and an animal to which the test fragrance has been applied and evaluating the difference as the effectiveness of the test fragrance in the capability of recovering the skin barrier function.

Further, in the method of evaluation of the effectiveness of the capability of a fragrance to recover a skin barrier function according to the present invention, preferably the method of application of the test fragrance is by inhalation.

Further, the skin barrier function recovery and promotion agent according to the present invention contains as an active ingredient a fragrance deemed to be effective evaluated by the above methods of evaluation.

The embodiments of the present invention will now be explained in detail. The present invention provides a skin barrier function recovery and promotion agent and a method of evaluation of the same. Therefore, the explanation will be given divided into the skin barrier function recovery and promotion agent and the method of evaluation thereof.

Skin Barrier Function Recovery and Promotion Agent

The skin barrier function recovery and promotion agent of the present invention contains a specific fragrance effective for recovery and promotion of the skin barrier function so as to alleviate poor skin conditions arising from a reduction in the skin barrier function by inhalation in an effective amount for stimulation of the odor receptors or inhalation into the body through the respiratory tract. As the specific fragrances, single compounds of terpinyl acetate, phenethyl alcohol, and dimethoxymethylbenzene are exemplified. These may be used alone or together or combined with other fragrances, as multiple-ingredient fragrance compositions.

Further, as multiple-ingredient fragrance compositions, valerian, sweet violet, and rose fragrances may be exemplified. These give the effect of recovery or promotion of the skin barrier function of the present invention in the form of natural compositions or artificial compositions reproducing them based on results of analysis.

As the valerian fragrance of the present invention, it is possible to use an essential oil obtained by a known method, for example, steam distillation or solvent extraction, from the roots and stems of *Valeriana officinalis* or its closely related species *Valeriana officinalis L.* var *latifolia Miq.* (*V. japonica Makino*), *Valeriana fauriei forma yezoensis, Valeriana wallichii* D.C., etc. Further, the essential oil extracted from *Valeriana officinalis* and its closely related species is commercially available as valerian oil and kesso root oil (Japanese valerian oil). These may be used regardless of whether they are produced in Japan, China, Europe, or elsewhere.

Further, the valerian oil fraction obtained by vacuum distillation from the natural composition disclosed in Japanese Unexamined Patent Publication (Kokai) No. 1-254628 may also be used as the valerian fragrance according to the present invention.

Further, the modified valerian oil obtained by removing the aliphatic acids and other acidic ingredients causing an unpleasant odor, explained below, may also be used as the valerian fragrance according to the present invention.

The modified valerian oil may be obtained by removing the acidic ingredients, including aliphatic acid, by alkali treatment from valerian oil. In general, natural valerian oil contains at least one type and usually several types of aliphatic acids. In particular, it includes acetic acid and isovaleric acid.

As the method of production of the modified valerian oil, first the valerian oil containing the aliphatic acids is dissolved in an organic solvent, preferably ether. Then, an aqueous alkali solution is then added thereto and an extraction operation performed to extract and recover the acidic ingredients containing the aliphatic acids. As the alkali aqueous solution, it is possible to use any generally used in ordinary extraction operations, without regard as to being an inorganic base or organic base, but preferably of a sodium bicarbonate aqueous solution or an aqueous sodium hydroxide solution. In particular, it is preferable to extract with a sodium bicarbonate aqueous solution, then further extract with a sodium hydroxide aqueous solution. The organic solvent layer thus obtained is then dried over anhydrous magnesium sulfate etc., then the organic solvent is distilled off in vacuo to obtain the modified valerian oil stripped of its aliphatic acids.

The skin barrier function recovery and promotion effect of the modified valerian oil according to the present invention is not impaired by the alkali treatment and is greater than that of the valarian oil before treatment. Therefore, according to this method, it is possible to further enhance the skin barrier function recovery and promotion effect of valerian oil. Further, according to this method of production, it is possible to easily and inexpensively produce such a modified valerian oil and possible to provide a highly useful skin barrier function recovery and promotion agent.

Further, as the sweet violet fragrance according to the present invention, it is possible to use an essential oil obtained by a known method, for example, steam distillation or solvent extraction from the leaves or flower of Viola odorata L. or the trappings at the head space of its living flower or leaves. Further, sweet violet may be used, regardless of whether produced in France, in Japan, or elsewhere. Further, in the present invention, it is also possible to use sweet violet fragrance artificially reproduced based on the ingredients analyzed from naturally derived sweet violet essential oil or the trappings at the head space of its living flower or leaves.

Further, as the rose fragrance according to the present invention, it is possible to use known essential oils, that Is, standard commercial grades, for the present invention. Further, it is possible to use essential oil obtained by distillation, extraction, or other methods from natural roses. Further, it is possible to use a rose fragrance reproducing artificially the composition based on the ingredients analyzed from essential oil obtained from the flower of natural roses.

The skin barrier function recovery and promotion agent including the above specific fragrance may be made into a product by the inclusion of a vehicle, diluent, or other active ingredient normally used in fragrance products. It may be made into fragrance products such as a perfume, cologne, room freshener, and also cosmetics such as a lotion, cream, soap, toothpaste, aerosol product, or any other form generally used for and other general medicines such as fragrances. Further, it may be used for inhalants. The content of the specific fragrance in the skin barrier function recovery and promotion agent should be an amount giving a sufficient effect of recovery or promotion of the skin barrier function through inhalation. While this differs depending on the form of use and the medicine (fragrance), it is generally necessary to Include at least 0.01% by weight. If less than this content, the skin barrier function recovery and promotion effect sometimes cannot be obtained.

The composition containing such a fragrance according to the present invention is suitable for treatment of a reduction in skin barrier function or skin diseases etc. based on the same. Further, the skin barrier function recovery and promotion agent of the present invention can be applied, without the problem of side-effects.

The skin barrier function recovery and promotion composition according to the present invention may contain any cosmetically or pharmacologically acceptable carrier (e.g., alcohols such as benzyl alcohol, dimethyl sulfoxide (DMSO), dimethyl formide (DMF)), and optional conventional additives such as a humectant, a surfactant, a UV absorber, an antioxidant, a preservative, an antifungal agent, a coloring pigment, an extender pigment, etc.

The effectiveness of The skin barrier function recovery and promotion agent of the present invention may be evaluated by the following evaluation method.

Method of Evaluation

The model experimental animals usable in the present invention are those commonly used as experimental animals for various tests other than humans. Any animal may be used so long as in line with the object of the present invention, but usually rats, guinea pigs, rabbits, etc. are used.

The stress applied to these animals means stress established as effective means in this field of art and includes stress through restraint, stress through overcrowding, and stress through a novel environment. The application method of restraint stress may be based on, for example, the method described in Pare, W. F., Glavin, G. B., (1986), *Neurosci. Biobehav-Rev.* 10, p. 339 to 370. Summarizing this method for the case of use of rats, stress may be applied by wrapping the individual animals entirely in a flexible wire mesh etc. and immobilizing them for a predetermined period of time, while taking care not to inflict damage to the skin.

On the other hand, for overcrowding stress, in the case of mice, mice are usually raised five to a cage (17×28 $cm^2$). Stress may be applied by increasing the number of animals raised in the same cage, in particular, to ten animals.

Further, for novel environment stress, stress may be applied by moving the animal from its usual environment to a strange environment, for example, in the case of mice, moving mice raised with normally four other mice in a cage (17×28 $cm^2$) to an environment of one mouse per cage.

This stress should be applied for a time period sufficient to cause a state of stress in the animal. However, when the stress is insufficiently applied, its should be noted that it is sometimes not possible to significantly distinguish the capability for recovery of the skin barrier with that of control animals.

The animals subjected to stress in this way are subjected to means for reducing the skin barrier function after reaching a state of stress (i.e., the state where effects of stress can be seen). The means may be any method capable of reducing the skin barrier function efficiently. The format of the means does not matter. To cause this reduction, it is convenient to remove the corneal layer of the epidermis by tape stripping or remove the corneal layer by treatment with a surfactant (for example, sodium dodecyl sulfate (SDS)) or an organic solvent such as acetone. As the timing of treatment, in the case of rats, after about 12 hours from the end of the application of the stress is preferable in ensuring a sufficient state of stress to the experimental animals.

The degree of recovery of the skin barrier function at the location of reduction of the skin barrier due to the above is detected over time or after a predetermined time interval. The location where the reduction is caused may be any location of the experimental animals so long as it enables detection of the degree of recovery of the skin barrier function, but usually it is preferable to select the auricle, that is, the projecting outer portion of the ear.

The method of detection may be to measure the transepidermal water loss or the transdermal insensible perspiration (hereinafter called the "TEWL")—generally considered an indicator of the skin barrier function, but it might be possible to use other factors capable of serving as indicators as well. The TEWL may be measured by a commercially available equipment itself in common use. As typical equipment, an Evaporimeter, a Tevameter, Micomoisture measurer, etc. may be mentioned.

According to the present invention, the above operation is repeated on experimental animals not subjected to stress and the similarly obtained TEWL values are compared with the above TEWL values of the experimental animals subjected to the stress. Note that, when, for example, using rats as the experimental animals, no significant difference could be observed in the TEWL and epidermal temperature of experimental animals subjected to stress and not subjected to stress before the reduction of the skin barrier function. Further, no gender difference could be observed in the TEWL values of the experimental animals.

That is, no correlation could be observed between the stress and the TEWL values of the experimental animals. Specifically, the degree of recovery of the above TEWL values was significantly delayed in animals subjected to stress according to the present invention compared with the control animals. Therefore, according to the present invention, it is possible to evaluate the capability of recovering the skin barrier function, based on the phenomenon of the delay of the degree of recovery.

Further, according to the present invention, it is possible to use a fragrance in combination with the above method of evaluation, to thereby evaluate how a fragrance helps to promote the skin barrier function or promote its recovery by evaluating the degree of recovery of the skin barrier function due to the fragrance. The method of application of a test fragrance to mice may be to cause inhalation of a sufficient amount capable of causing an effect over a sufficient time, but specifically, in, for example, the case of strange environment stress, the fragrance is dropped onto filter paper placed in a Petri dish which is, then, covered with a wire mesh and placed in a rouse cage. The mouse is made to inhale the fragrance for 24 hours, before and after being transferred to the strange environment. Note that if necessary, more of the fragrance is preferably added. According to this evaluation method, it is possible to evaluate if a certain specific fragrance has an action for recovery of the skin barrier function reduced by stress or promotion of the function and to evaluate fragrances useful for improvement of skin conditions.

EXAMPLES

The present invention will now be further illustrated by, but is by no means limited to, the following Examples. First, Examples of the evaluation method of a skin barrier function recovery and promotion agent of the present invention will be explained.

Example 1
Application of Novel Environment stress

Five hairless mice were raised for 10 days in a single cage (17×28 cm$^2$). On the morning of the ninth day, a filter paper impregnated with a fragrance was placed in the cage covered with a stainless steel mesh. The next morning, each mouse was moved separately to a new cage of the same size. The same fragrance had been placed beforehand in the same way in the new cages.

Example 2
Reduction of Spin Barrier and Rate of Recovery

After one day after transfer to the new cages, the TEWL values of the flanks for auricles) of the anesthetized mice were measured by an Evaporimeter EP-1 (ServoMed Co.) (i.e., the values measured at this time were designated as "AD"). Next, the skin barrier functions were reduced by tape stripping. That is, pieces of adhesive tape were adhered to the flanks (or auricles) of the animals (1×1 cm$^2$ in the case of the ears and 2×3 cm$^2$ in the case of the flank (or torso)) and the pieces of tape were carefully peeled off (i.e., tape stripping) to cause a reduction in the skin barrier function, without causing damage to the epidermis. The TEWL values were measured once more at this time (i.e., the values measured being designated as "B"). After 3 hours, the TEWL values were measured and the measured values designated as "C". Then, the rate of recovery of the barrier was calculated by the following formula:

Barrier recovery rate (%)=[((B-C)/(B-A)]×100

A: TEWL value immediately before the treatment of the reduction in the skin barrier function (i.e., tape stripping)
B: TEWL value immediately after the treatment of the reduction in the skin barrier function (i.e., tape stripping)
C: TEWL value after a given time period from the treatment of the reduction in the skin barrier function (i.e., tape stripping)

Figure 1:
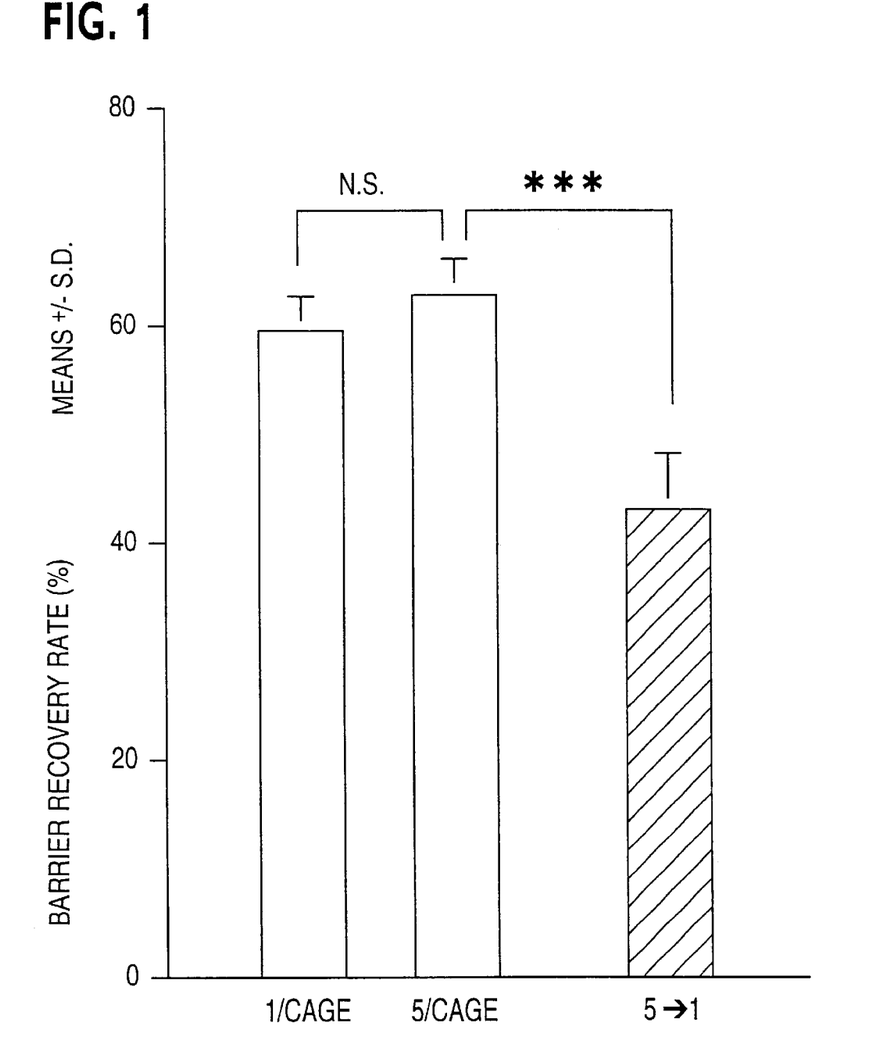
FIG. 1 is a graph illustrating the effect of the application of stress by a strange environment on the degree of skin barrier function recovery.

Next, the effect of the application of stress by the strange environment on the degree of recovery of the skin barrier function was examined according to the above-methods 1 and 2. Animals continued to be raised one to a cage (i.e., control animals), animals continued to be raised five to a cage (i.e., control animals), and animals transferred from five- to one-animal cages (i.e., animals subjected to stress) were treated to reduce their skin barrier functions. The converted barrier recovery rates after the elapse of 3 hours from the treatment are shown in FIG. 1. Note that the experiment was conducted in systems with no fragrance.

From the FIG. 1, it is recognized that the degree of recovery of the skin barrier function of the animals subjected to stress was significantly slower than the degree of recovery of the control animals.

Example 3
Effect of Fragrance on Degree of Recovery of Skin Barrier Function The effectiveness of a fragrance on the recovery and promotion of the skin barrier function was evaluated, after application of the stress of Example 1 to hairless mice in the presence of the test fragrance, in the rate of recovery of the skin barrier of Example 2.

Next, the barrier recovery rate after 3 hours from tape stripping was measured as explained above to check the effectiveness.

Note that as Control Experiments, the barrier recovery rate was measured in the system containing no fragrance in the same way for normal mice continued to be raised five to a cage and not subjected to stress and untreated mice subjected to stress, but then not made to inhale the fragrance.

Next, an explanation will be made of skin barrier function recovery and promotion agents containing as active ingredients the fragrances confirmed to have effectiveness by the above method of evaluation.

Single Compounds (Single Chemicals)

Figure 2:
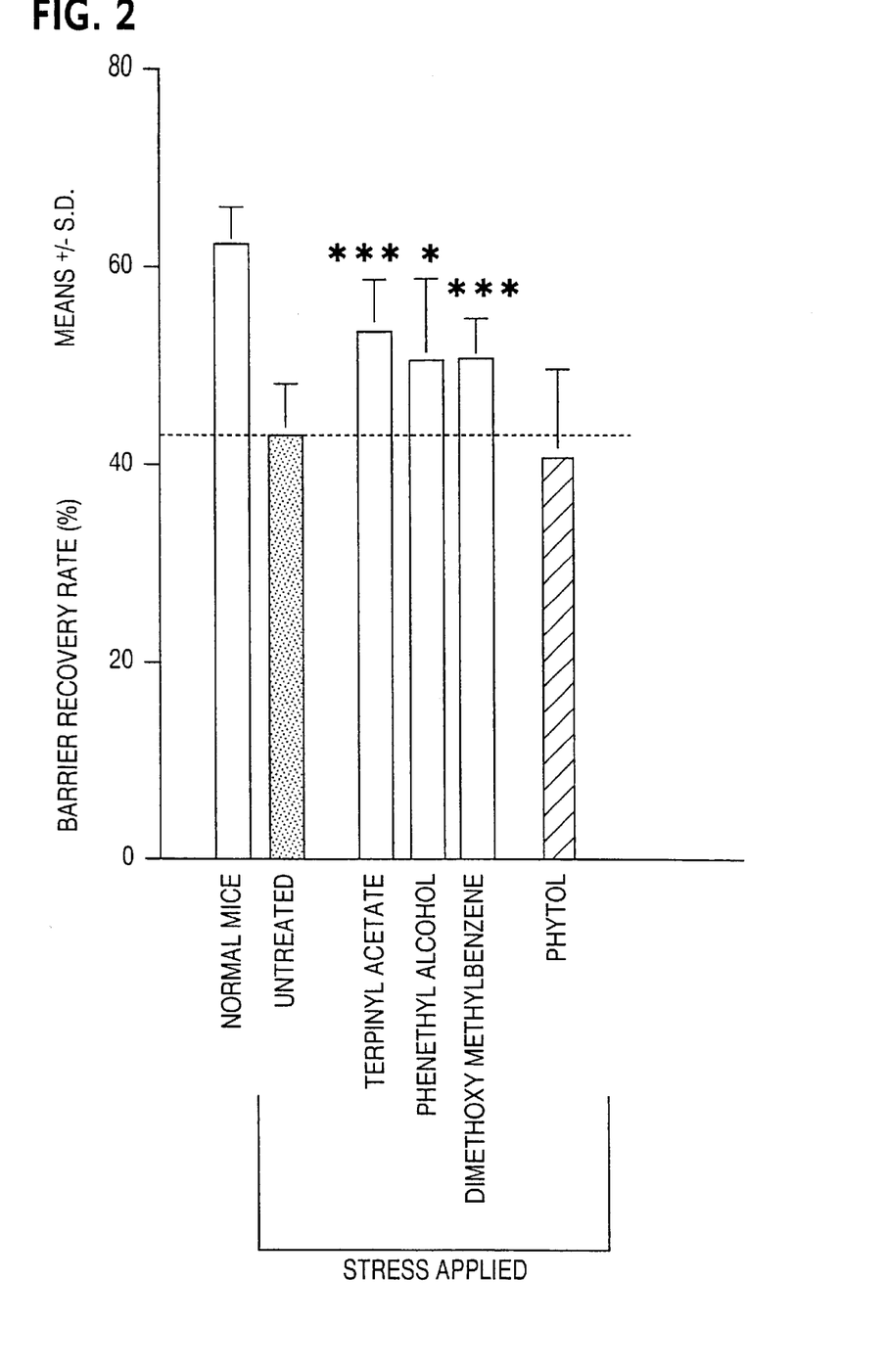
FIG. 2 is a graph illustrating the results of recovery from reduction of the skin barrier function with a fragrance (single compound) and further promotion of the recovery ability.

The skin barrier recovery rates of single compounds obtained by the method of evaluation of Example 3 are shown in FIG. 2. The results are shown in Table 1. Note that, as a Comparative Control Experiment the same procedure was performed for the main ingredient of the jasmine fragrance, phytol. The amounts of inhalation of the fragrances by mice were made substantially uniform by coating 200 μl portions of each single compound on filter paper in Petri dishes.

TABLE 1

| Fragrance (single compound) | Skin barrier function recovery and promotion effect |
| --- | --- |
| Terpinyl acetate | Yes |
| Phenethyl alcohol | Yes |
| Dimethoxymethylbenzene | Yes |
| Phytol | No |

As is clear from FIG. 2, an effect of recovery and promotion of the skin barrier function was obtained, compared with untreated mice, in terpinyl acetate, phenethyl alcohol, and dimethoxymethylbenzene. Further, no skin barrier function recovery effect could be obtained for the main ingredient of a jasmine fragrance, i.e., phytol.

Therefore, it was learned that terpinyl acetate, phenethyl alcohol, and dimethoxymethylbenzene are effective as skin barrier function recovery and promotion agents.

Fragrance Compositions (Fragrance Compounds)

Figure 3:
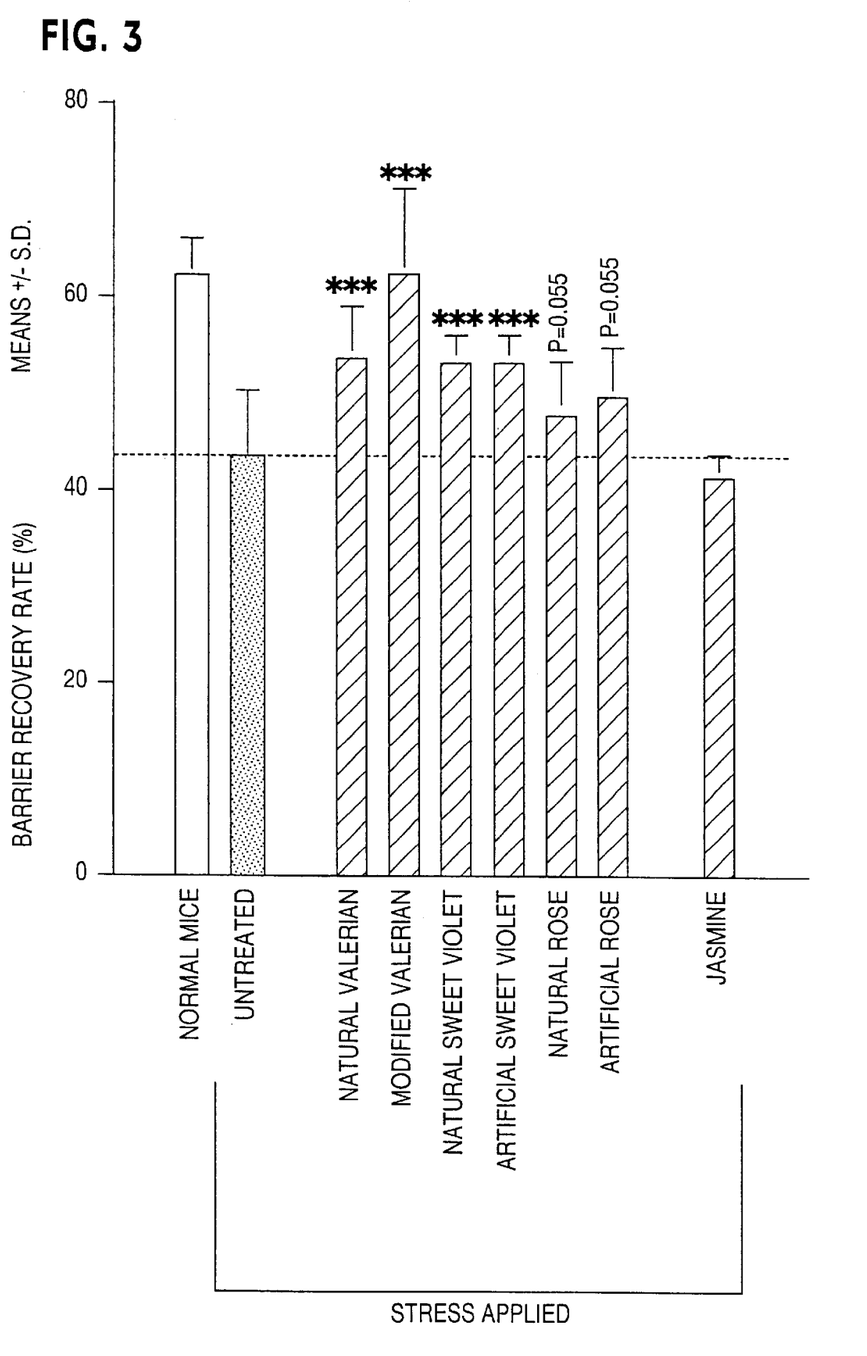
FIG. 3 is a graph illustrating the results of recovery from reduction of the skin barrier function by a fragrance (composition) and further promotion of the recovery ability.

Next, the skin barrier recovery rates of multiple-ingredient based compositions obtained by the method of evaluation of Example 3 are shown in FIG. 3. The results are shown in Table 2. Note that the amounts of inhalation of the fragrance compositions by mice were made substantially uniform by coating 200 µl portions of each single compound on filter paper in Petri dishes. As a Comparative Control Experiment, the same procedure was performed for jasmine having phytol as a main ingredient (14 to 15%).

TABLE 2

| Fragrance (composition) | Skin barrier function recovery and promotion effect |
|---|---|
| Natural valerian | Yes |
| Modified valerian | Yes |
| Natural sweet violet | Yes |
| Artificial sweet violet | Yes |
| Natural rose | Yes |
| Artificial rose | Yes |
| Natural jasmine | No |

In the Table, for the valerian fragrance, natural essential oil and the above-explained modified valerian were used.

Figure 4:
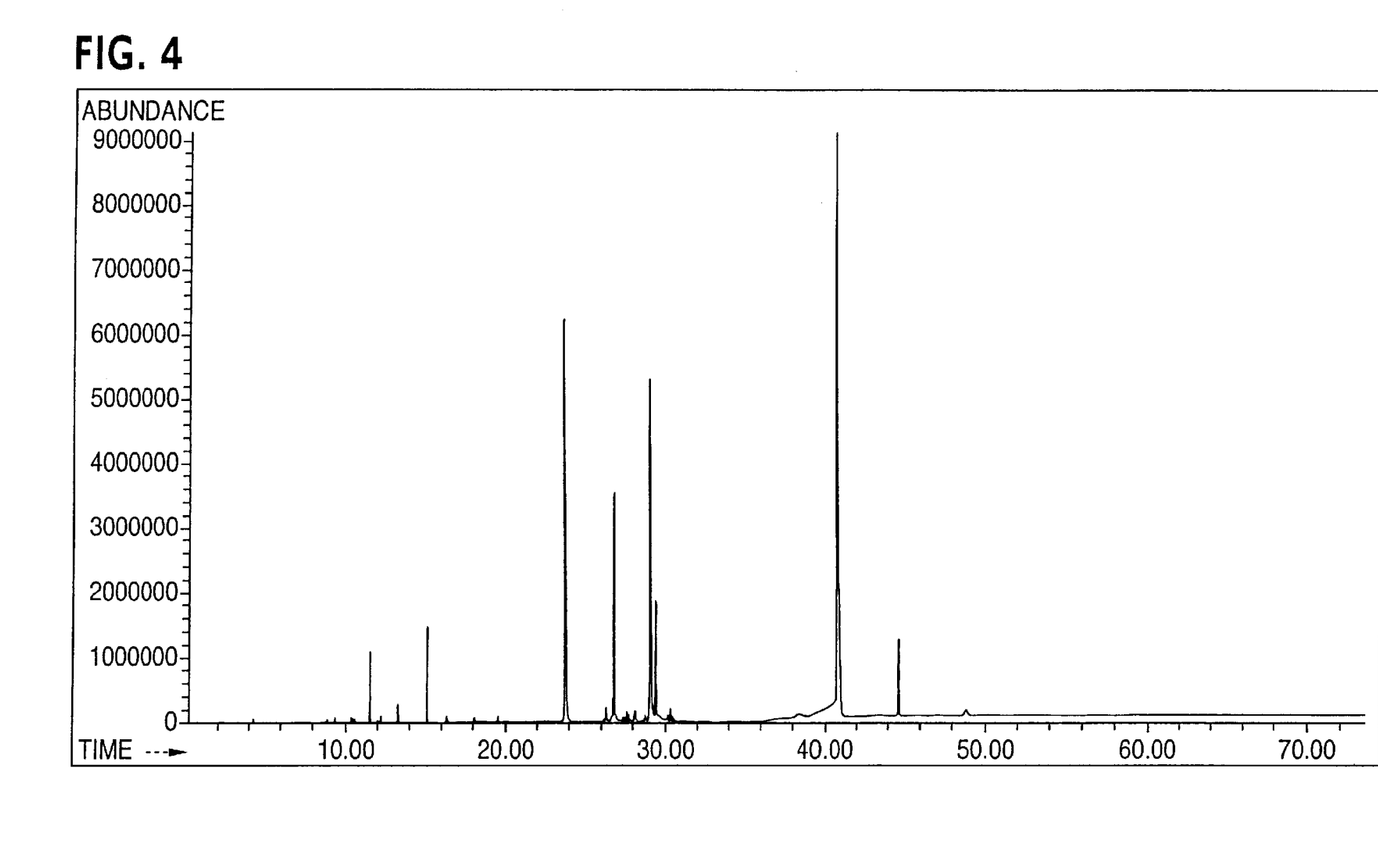
FIG. 4 is a chart of the gas chromatography of artificial sweet violet fragrance.

Further, the natural sweet violet fragrance used was a sweet violet essential oil derived from the flower. The artificial sweet violet fragrance used was a composition combining the single compounds contained to reproduce the natural essential oil based on analysis by gas chromatography and mass spectroscopy (GC-MS) of the oil. FIG. 4 is a chart of the gas chromatography of the reproduced fragrance composition. Table 3 shows the composition obtained as a result. Note that the GC-MS measurement conditions were as follows:

GC-MS Analysis Condition

Model: G1800A GCD (made by Hewlett-Packard Co., Ltd.)

Column: HP-INNOWAX (60 m×0.25 mm) (made by Hewlett-Packard Co., Ltd.)

Column temperature: 70→245° C. (4° C./min rise)

Carrier gas: He (1.0 ml/min)

TABLE 3

| Name of compound | GC content (%) |
|---|---|
| Limonene | 0.16 |
| Trans-2-hexenal | 0.18 |
| 1-hexyl acetate | 0.23 |
| cis-3-hexenyl acetate | 3.09 |
| trans-2-hexenyl acetate | 0.11 |
| 1-hexanol | 0.28 |
| p-cymene | 0.16 |
| cis-3-hexenol | 0.78 |
| 1-octen-3-ol | 4.36 |
| 2-ethylhexanol | 0.34 |
| Linalol | 0.21 |
| trans, cis-2,6-nonadyl | 0.21 |
| 1,4-dimethoxybenzene | 23.01 |
| Neryl acetone | 0.12 |
| Dihydro-β-ionone | 0.87 |
| α-Ionone | 13.29 |
| 2-phenylethanol | 0.67 |
| β-Ionone | 22.23 |
| cis-jasmone | 3.73 |
| Methyl jasmonate | 2.09 |
| Benzyl benzoate | 4.56 |
| Total | 80.70 |

Further, the natural rose fragrance used was the natural general commercially available rose essential oil. The artificial rose fragrance used was a fragrance composition containing dimethoxymethylbenzene and phenethyl alcohol, compounds recognized as having a skin barrier function recovery and promotion effect. The artificial. rose fragrance was comprised of the following composition. Note that amounts are parts by weight.

TABLE 4

| Artificial rose fragrance | Parts by weight |
|---|---|
| Dimethoxymethylbenzene | 5 |
| Phenethyl alcohol | 200 |
| cis-3-hexenol | 1 |
| cis-3-hexenyl acetate | 2 |
| Benzyl alcohol | 15 |
| Citronellol | 100 |
| Nerol | 25 |
| Geraniol | 600 |
| Geranyl acetate | 20 |
| Citronellyl acetate | 4 |
| Citral | 3 |
| Eugenol | 5 |
| Farnesol | 40 |
| Total | 1020 |

As is clear from FIG. 3, it is learned that the skin barrier recovery rates of fragrance compositions of valerian and sweet violet and further rose are higher, compared with untreated mice not made to inhale the fragrance. Further, referring to the result for sweet violet and rose fragrances, it is learned that the skin barrier recovery rate is obtained, regardless as to if the fragrance composition effective for recovery of the skin barrier function is natural or artificial. Further, turning to valerian, modified valerian gives a skin barrier recovery rate as high as the same extent as that of normal mice and is found to be particularly superior. Note that jasmine, which is known to be effective against skin diseases as well in aromatherapy, failed to show a skin barrier function recovery effect.

Therefore, it is learned that valerian, sweet violet, and rose fragrance compositions are superior as skin barrier function recovery and promotion agents. Further, it was learned that the effect exists, regardless of whether the fragrance is natural or artificial, as shown by the sweet violet and rose fragrances. On the other hand, referring to the jasmine, it was learned that, even a fragrance exhibiting effectiveness against the skin in aromatherapy does not necessarily give a skin barrier function recovery effect.

Then, the present inventors investigated the effect of the skin barrier function recovery and promotion agent on humans. This was done for three cases: the case of no other fragrance added and normal condition, the case of another fragrance added and normal condition, and the case of another fragrance added and the skin barrier recovery rate made to decline.

Case of No other Fragrance Added and Normal Condition (No stress Applied)

Six men (nonsmokers) were used as test subjects. The measurement was carried out by dividing them into two groups of three each of "fragrance" and "no fragrance". After once measuring the entire samples, the test subject groups for the "fragrance" and for the "no fragrance" were changed with each other and the same measurements were carried out. The application method of the fragrance was to adhere a piece of cotton containing 80 µl of a solution of the following Sample 1 below the nose. In the case of "no skin barrier function recovery and promotion agent", just a piece of cotton was adhered there.

Sample 1

| | parts by weight |
|---|---|
| Dimethoxymethylbenzene (DMMB) | 2.0 |
| Ethanol (brucine modified 95% ethanol) | 98.0 |
| Total | 100.0 |

Measurement Procedure

The procedure for measurement of the "fragrances" group was to start the application of the fragrance, break the skin barrier by tape stripping after 1 hour under an environment of 22° C. and a humidity of 50%, then measure the skin barrier recovery rate after 1.5 hours and after 3 hours according to Example 2. The fragrance continued to be applied and the environment maintained until the end.

The procedure for measurement of the "no fragrance" group was to measure the skin barrier recovery rate without application of the fragrance according to the procedure for measurement of the "fragrance" group.

The results are shown in the following Table.

TABLE 5

| | | After 1.5 hours | | After 3 hours | |
|---|---|---|---|---|---|
| Group name | After 0 hour | Average | Standard deviation | Average (n = 6) | Standard deviation |
| No fragrance | 0% | 50.8% | 8.00% | 61.3% | 11.09% |
| Fragrance | 0% | 63.1% | 8.63% | 74.5% | 8.78% |

From the results of the above Table, it is learned that the skin barrier recovery rate was higher with the DMMB fragrance both 1.5 hours and 3 hours after the breakage of the skin barrier. Therefore, it is clear that DMMB has a skin barrier function recovery and promotion effect.

Case of Other Fragrance Added and Normal Condition (No Stress Applied)

Ten healthy women having an age of 20 to 22 (nonsmokers, menstrual cycles confirmed) were used as test subjects. The measurement was carried out by dividing them into two groups of five each of "fragrance" group and "no fragrance" group. After once measuring the entire samples, the test subject groups for the "fragrance" and for the "no fragrance" were changed with each other and the same measurement were carried out. The application method of the fragrance was to adhere a piece of cotton containing 80 µl of a solution of the following Sample 2 below the nose. In the case of no fragrance, just a piece of cotton was adhered there.

Sample 2

| | parts by weight |
|---|---|
| Citronellol | 5.0 |
| Linalol | 4.0 |
| Linalyl acetate | 4.0 |
| Dimethoxymethylbenzene (DMMB) | 2.0 |
| Geranyl acetate | 1.0 |
| Dihydromethyl jasmonate | 35.0 |
| Floral base fragrance | 49.0 |
| Total | 100.0 |

Measurement Procedure

The procedure for measurement of the "fragrance" group was to start the application of the fragrance, break the skin barrier by tape stripping after 1 hour under an environment of 22° C. and a humidity of 50%, then measure the skin barrier recovery rate after 1.5 hours and after 3 hours in accordance with Example 2. The fragrance continued to be applied and the environment maintained until the end.

The procedure for measurement of the "no fragrance" group was to measure the skin barrier recovery rate without application of the fragrance according to the procedure for measurement of the "fragrance" group.

Figure 5:
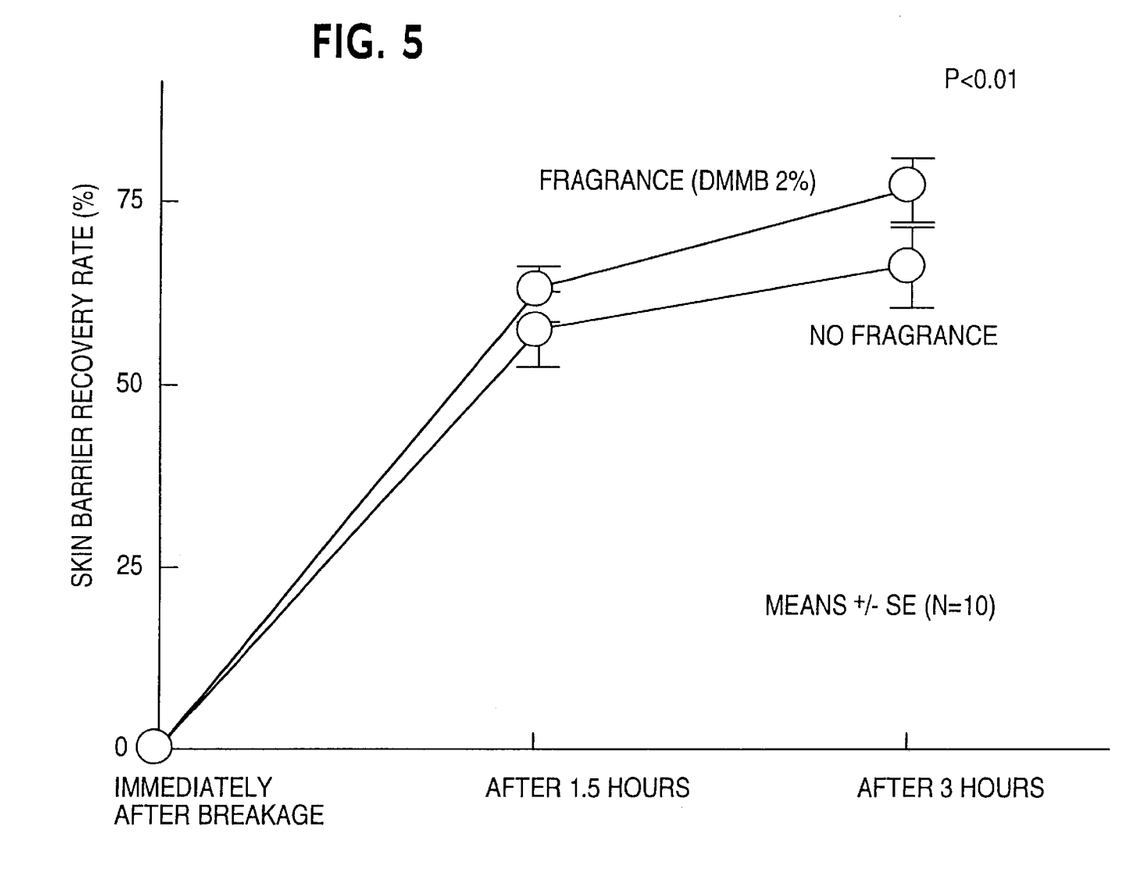
FIG. 5 is a view of the effect of the skin barrier function recovery and promotion agent of the present invention in the case where no stress is applied.

The results are shown in Table 6 and FIG. 5.

TABLE 6

| | | After 1.5 hours | | After 3 hours | |
|---|---|---|---|---|---|
| Recovery rate | After 0 hour | Average | Standard deviation | Average (n = 10) | Standard deviation |
| No fragrance | 0% | 58.1% | 14.6% | 67.4% | 14.7% |
| Fragrance | 0% | 63.1% | 10.9% | 78.3% | 11.2% |

As shown in Table 6 and FIG. 5, it was learned that the "fragrance" group provided with the fragrance composition containing DMMB exhibited an improved recovery rate of the skin barrier function, when compared with "no fragrance".

Next, the effect of a fragrance composition containing DMMB on the stress level was investigated by the degree of subjective stress (General Activity Check List).

Figure 6:
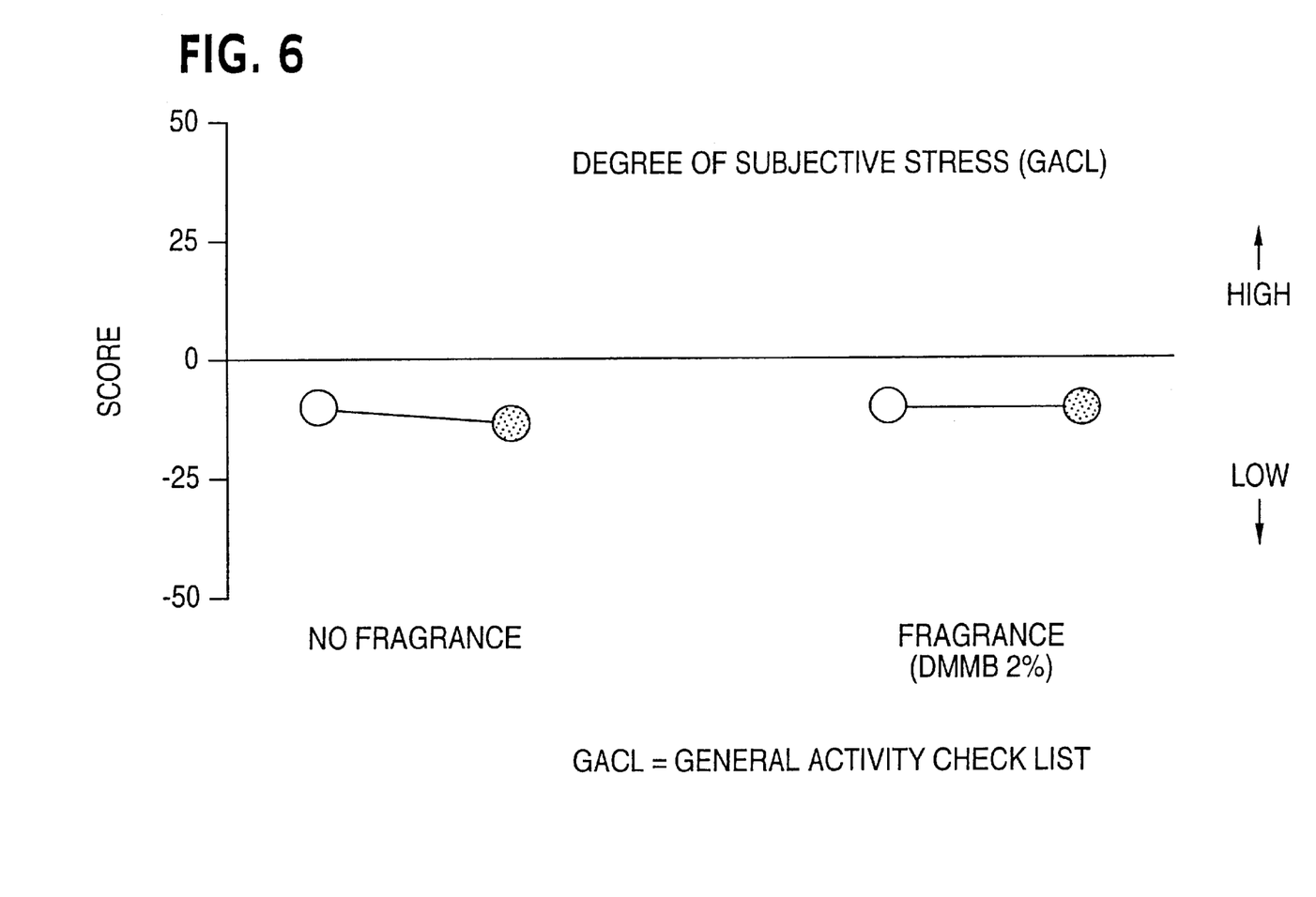
FIG. 6 is a view of the effect of the skin barrier function recovery and promotion agent of the present invention on the stress level in the case where no stress is applied.

The results are shown in FIG. 6. AS shown in FIG. 6, no reduction in stress at all was seen in "fragrance", when compared with "no fragrance" in terms of score. Therefore, it was learned that the skin barrier function recovery and promotion agent does not have that much of any effect on the subjective stress.

Case of Skin Barrier Function Made to Decline (Stress Applied)

Eight healthy women of age 20 to 22 (nonsmokers, menstrual cycles confirmed) were used as test subjects. The measurement was carried out by dividing them into three groups of (A) control, (B) stress, and (c) fragrance+stress as shown in the following Table 7. After once measuring the entire test samples, each test subject was changed with each other and finally the test subjects carried out all the measurements of (A), (B) and (c).

TABLE 7

| Group name | Stress | Fragrance |
|---|---|---|
| (A) Control | No | No |
| (B) Stress | Yes | No |
| (C) Fragrance + Stress | Yes | Yes (sample 2: DMMB 2%) |

The fragrance was applied in the same way as with the above "case of other fragrance added and normal condition". Note that all of the tests were conducted under an environment of 22° C. and 50% humidity.

Measurement Procedure

The procedure for measurement of the group (A) was based on the "no fragrance" group in the above-mentioned "case of other fragrance added and normal condition".

The procedure for measurement of the group (B) was based on the "no fragrance" group in the above-mentioned "case of other fragrance added and normal condition", but, starting from 1 hour before the measurement of the skin barrier recovery rate at the time of 1.5 hours after the breakage of the skin barrier by tape stripping, a Stroop test was conducted for 1 hour to apply stress and then the skin barrier recovery rate was measured.

The procedure for measurement of the group (C) was based on the "no fragrance" group of the above "case of other fragrance added and normal condition", but, starting from 1 hour before the measurement of the skin barrier recovery rate at the time of 1.5 hours after the breakage of the skin barrier by tape stripping, a Stroop test was conducted for 1 hour to apply stress and then the skin barrier recovery rate was measured.

Figure 7:
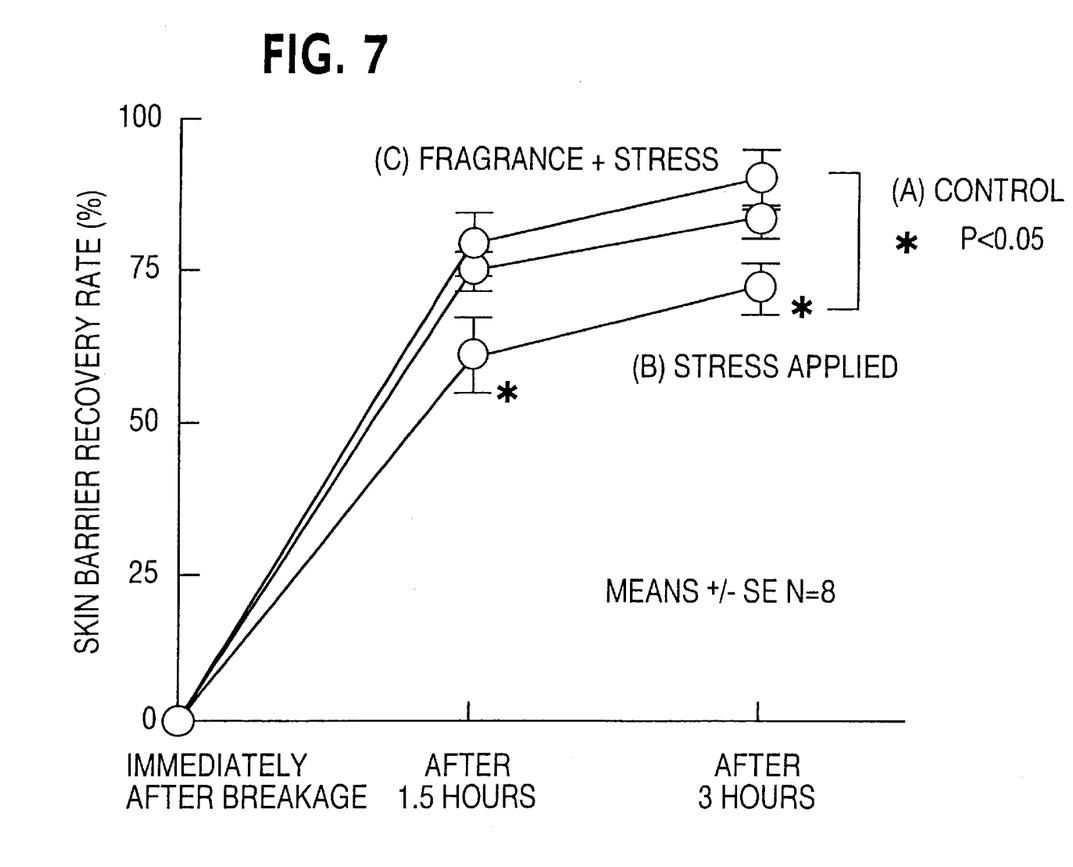
FIG. 7 is a view of the effect of the skin barrier function recovery and promotion agent of the present invention in the case where stress is applied.

The results are shown in Table 8 and FIG. 7.

TABLE 8

| | | After 1.5 hours | | After 3 hours | |
|---|---|---|---|---|---|
| Group name | After 0 hour | Average (n = 8) | Standard deviation | Average (n = 8) | Standard deviation |
| (A) Control | 0% | 73.6% | 8.89% | 81.6% | 8.80% |
| (B) Stress | 0% | 60.2% | 17.05% | 70.9% | 11.55% |
| (C) Fragrance + Stress | 0% | 78.2% | 15.95% | 88.5% | 14.28% |

As shown in Table 8 and FIG. 7, it was learned that the "(C) fragrance+stress" group subjected to stress and provided with the fragrance composition containing DUMB exhibited an improved recovery rate of the skin barrier, when compared with the "(B) stress" group. Further, the "(C) fragrance+stress" group exhibited a higher skin barrier recovery rate than even the "(A) control" group not subjected to stress, and therefore, it can be understood that the skin barrier function recovery and promotion agent according to the present invention is superior.

Next, the effect of a fragrance composition containing DMMB on the stress level was investigated by the degree of subjective stress (General Activity Check List).

Figure 8:
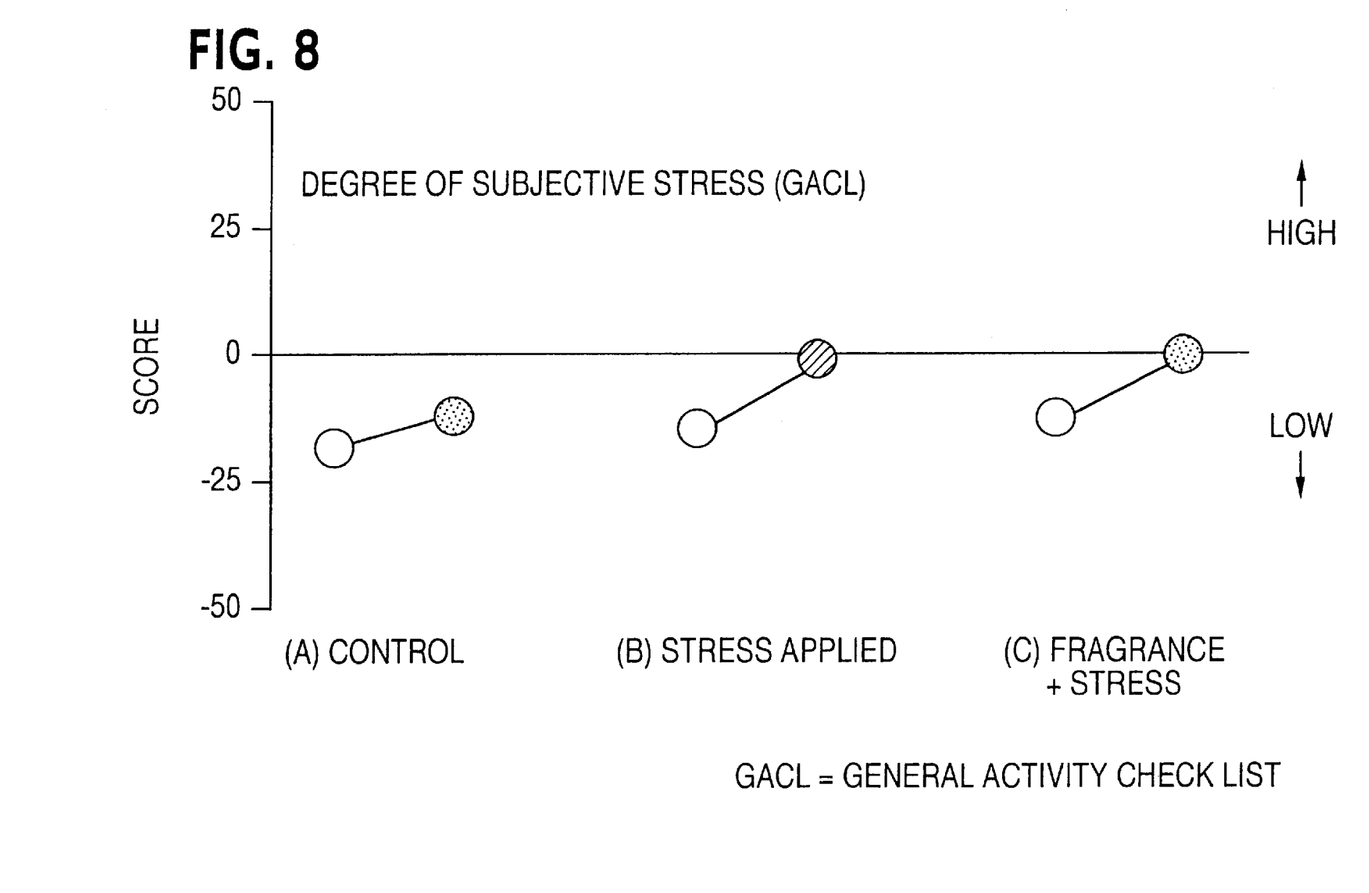
FIG. 8 is a view of the effect of the skin barrier function recovery and promotion agent of the present invention on the stress level in the case where stress is applied.

The results are shown in FIG. 8. As shown in FIG. 8, no reduction in stress at all was seen in the "(C) fragrance+stress" group, when compared with the "(B) stress" group in terms of score. Therefore, it was learned that the skin barrier function recovery and promotion agent does not substantially affect the subjective stress.

As explained above, the skin barrier function recovery and promotion agent of the present invention can give a superior effect of recovery and promotion of the skin barrier function since fit contains a specific fragrance.

Further, according to the evaluation method of the present invention, an objective and simple method of evaluation is provided for the effect on the skin barrier function in fragrances. This evaluation method can be used for development of skin condition improving fragrances.

Further, the fragrances confirmed as effective by this evaluation method are effective as skin barrier function recovery and promotion agents and improve the skin diseases due to reduction of the skin barrier function.

What is claimed is:

1. A method for evaluating the effectiveness of the capability of a test fragrance to recover a skin barrier function comprising:

(i) applying a predetermined stress to an experimental animal in a system wherein the test fragrance is not applied, reducing the skin barrier function of the experimental animal, determining the degree of recovery of the reduced skin barrier function, from which data is obtained and indicatively used for evaluation;

(i) applying a predetermined stress to an experimental animal in a system wherein the test fragrance is applied, reducing the skin barrier function of the experimental animal, determining the degree of recovery of the reduced skin barrier function, from which data is obtained and indicatively used for evaluation; and (iii) evaluating the data obtained from both steps (i) and (ii).

2. A method as claimed in claim 1, wherein the method of application of the fragrance is by inhalation.

3. A method as claimed in claim 1, wherein the experimental animal is a mouse, rat or guinea pig, and wherein the degree of recovery of the reduced skin barrier function is determined by measuring the transepidermal water loss (TEWL) in a reduced location at constant times.

* * * * *